United States Patent
Lodato et al.

(10) Patent No.: US 10,905,326 B1
(45) Date of Patent: Feb. 2, 2021

(54) METHOD AND APPARATUS FOR ACQUIRING AND COLLECTING BIOMETRIC DATA SENSED AT A USER'S CHIN

(71) Applicant: VSN MOBILE, INC., Fort Lauderdale, FL (US)

(72) Inventors: Franco Lodato, Weston, FL (US); Gustavo Leizerovich, Aventura, FL (US); Jose Ruiz, Coral Springs, FL (US); Biren Patel, Coral Springs, FL (US); Hao Nguyen, Lake Worth, FL (US)

( * ) Notice: Subject to any disclaimer, the term of this patent is extended or adjusted under 35 U.S.C. 154(b) by 909 days.

(21) Appl. No.: 14/807,416

(22) Filed: Jul. 23, 2015

Related U.S. Application Data (63) Continuation-in-part of application No. 14/674,141, filed on Mar. 31, 2015.

(51) Int. Cl.
| | |
|---|---|
| *A61B 5/00* | (2006.01) |
| *H04Q 9/00* | (2006.01) |
| *H04W 84/18* | (2009.01) |

(52) U.S. Cl.
CPC ............ *A61B 5/0015* (2013.01); *H04Q 9/00* (2013.01); *H04Q 2209/40* (2013.01); *H04W 84/18* (2013.01)

(58) Field of Classification Search
CPC .......... G08B 23/00; G08B 21/02; G09B 5/08
USPC .......... 340/573.1; 434/247; 702/41; 713/171
See application file for complete search history.

(56) References Cited

U.S. PATENT DOCUMENTS

| | | | |
|---|---|---|---|
| 6,585,622 B1 * | 7/2003 | Shum ................. | A63B 24/0084 482/8 |
| 6,602,191 B2 * | 8/2003 | Quy ..................... | A61B 5/7465 128/903 |
| 6,893,396 B2 * | 5/2005 | Schulze ............. | G06F 19/3418 128/903 |
| 8,162,804 B2 * | 4/2012 | Tagliabue ........... | G01C 22/006 482/8 |
| 8,702,430 B2 * | 4/2014 | Dibenedetto ..... | H04M 1/72563 434/247 |
| 8,938,368 B2 * | 1/2015 | Yuen .................... | A61B 5/6838 702/155 |
| 9,070,269 B2 * | 6/2015 | Evans .................... | G08B 21/02 |
| 9,819,754 B2 * | 11/2017 | Park ..................... | A61B 5/0002 |
| 2007/0159926 A1 * | 7/2007 | Prstojevich ........... | G04G 19/12 368/10 |

(Continued)

OTHER PUBLICATIONS

Stack, Kyle "Concussion-Sensing Chin Strap Raises Questions". Mar. 26, 2012 http://www.wired.com/2012/03/battle-sports-science-indicator.

*Primary Examiner* — Albert K Wong
(74) *Attorney, Agent, or Firm* — Patents on Demand P.A.; Brian K . Buchheit (57) ABSTRACT

A method and apparatus for collecting and evaluating biometric data of members of a group uses a mobile ad hoc network to relay information collected from each group member to a monitoring device. The information is collected from each group member using a chin strap biometric sensing device. The monitoring device is an endpoint of the mobile ad hoc network, and organizes the collected data for evaluation and display to a supervisor of the group. Any biometric parameter for a given group member that exceeds a preferred value can be flagged for immediate attention by the supervisor.

20 Claims, 4 Drawing Sheets

(56) References Cited

U.S. PATENT DOCUMENTS

| | | | |
|---|---|---|---|
| 2008/0103794 A1* | 5/2008 | Pettiross | G06Q 30/02 705/2 |
| 2011/0181419 A1* | 7/2011 | Mack | A42B 3/046 340/573.1 |
| 2014/0248595 A1* | 9/2014 | Crabtree | G09B 5/08 434/247 |

\* cited by examiner

METHOD AND APPARATUS FOR ACQUIRING AND COLLECTING BIOMETRIC DATA SENSED AT A USER'S CHIN

CROSS REFERENCE

This application claims the benefit of prior U.S. patent application Ser. No. 14/674,141 filed Mar. 31, 2015, and titled "Method and Apparatus for Acquiring and Collecting Biometric Data for a Group Engaged in a Common Activity," the entirety of which is hereby incorporated by reference.

FIELD OF THE DISCLOSURE

The present disclosure relates generally to real time biometric sensing and evaluation, and more particularly to the collection of biometric data by sensing at the user's chin.

BACKGROUND

There are a number of biometric sensing devices in use that sense biometric parameters of a person and format the sensed data for display, such as being displayed by a graphical user interface, or by audio signals, or both. Such devices are generally limited in what parameters they sense and record as well as what the person whose biometric parameters are being sensed can do while the sensing is occurring. In medical settings, for example, a patient typically remains stationary or has very limited mobility during a measurement process. In response, there have been biometric sensing devices designed that allow personal mobility, such as devices that sense at the user's wrist, or around the user's chest. While allowing more mobility than stationary sensing system, these configurations still limit a user's activity and preclude some more vigorous activity such as contact sports.

Furthermore, biometric sensing devices often communicate information to other devices in a non-mobile application where the subject whose biometric parameters are being sensed does not have much, if any, mobility. Conversely, in mobile sensing arrangements, where the subject is mobile (e.g. jogging), a conventional sensing device does not communicate beyond the user while the sensing is occurring. Additionally there is no present system that allows for the collecting and managing of the biometric data of members of a group of people engaged in a common activity.

Accordingly, there is a need for a method and system for sensing, collecting, and transmitting biometric data that can be used in rugged applications such as contact sports, and which allow collection of biometric information of all members of the group cooperatively.

BRIEF DESCRIPTION OF THE FIGURES

In the accompanying figures like reference numerals refer to identical or functionally similar elements throughout the separate views, together with the detailed description below, and are incorporated in and form part of the specification to further illustrate embodiments of concepts that include the claimed invention and explain various principles and advantages of those embodiments.

Those skilled in the field of the present disclosure will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The apparatus and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. The details of well-known elements, structure, or processes that would be necessary to practice the embodiments, and that would be well known to those of skill in the art, are not necessarily shown and should be assumed to be present unless otherwise indicated.

DETAILED DESCRIPTION

Embodiments included in the disclosure include a mobile ad hoc network-based biometric collection and reporting system for a group. The system includes a plurality of chin strap biometric sensing devices. Each of the chin strap biometric sensing devices are configured to be worn by a member of the group, and to collect biometric data of the respective member of the group. Furthermore each chin strap biometric sensing device includes a network transceiver to transmit and relay collected biometric data via a network that is established by the plurality of chin strap biometric sensing devices, where each one acts as a node of the network. The system also includes a monitoring device that communicates with the network to receive the biometric data of each member of the group via the network. The biometric data is received in a generally real time manner, and the monitoring device organizes the biometric data for display to a supervisor of the group by group member.

In similar embodiments the monitoring device can be linked to a backend server that can store biometric data and the results of processing biometric data such as trends, totals, averages, and so on of various biometric parameters for each of the group members. The biometric data and processed data can be distributed to various individuals who supervise different aspects of the group, such as, for example, performance or health. In some embodiments the biometric data can be made available to third parties.

Figure 1:
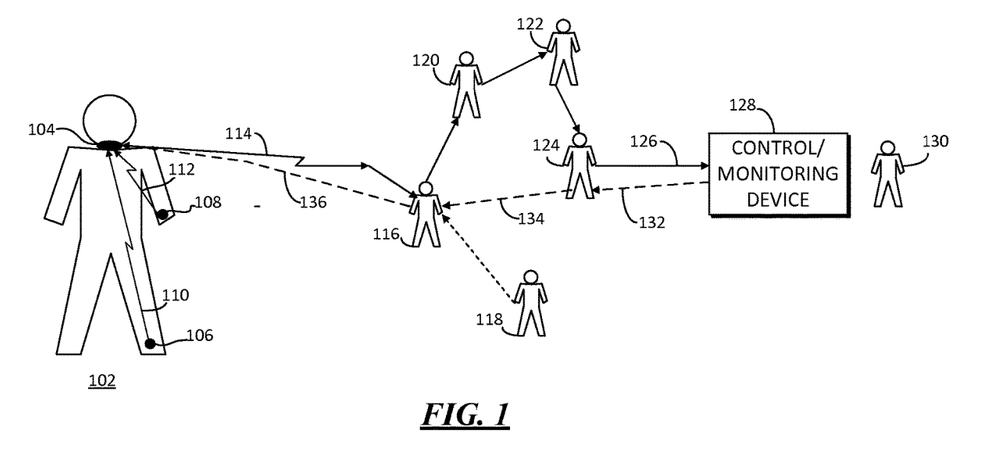
FIG. 1 is a system diagram of a biometric data collection and evaluation system for a group engaged in an activity, where the biometric sensing is performed at the chin of each member of the group, in accordance with some embodiments.

FIG. 1 is a system diagram of a biometric data collection and evaluation system 100 suitable for use with a group engaged in an activity, where the biometric sensing is performed at the chin of each member of the group, in accordance with some embodiments. The group includes group members such as group member 102, and group members 116, 118, 120, 122, 124. Each member of the group wears a biometric sensing device such as chin strap biometric sensing device 104. The group members can be engaged in an activity such as an athletic event, a public safety action, a military action, and so on. Generally, biometric data of each group member is communicated to a control/monitoring device 128, which acts as a collection point for biometric data, which is in turn made available to a supervisor 130 who supervises the group. The control/monitoring device 128 can also be used by the supervisor 130 to issue commands to the chin strap biometric sensing devices (i.e. 104), such as a prompt to transmit information about the wearer, including recently collected biometric data, which can include data for one or more biometric parameters. The supervisor 130 can be, for example, a coach, a health supervisor, a commander, or other person in a similar supervisory role. The supervisor 130 can make decisions based on the data being received for each group member at the monitoring device 128. In addition to the biometric data, the chin strap biometric devices (e.g. 104) can also collect other data, such as location data, data derived from location data (e.g. maximum speed, total distance moved, etc.) and performance data, and forward such information to the monitoring device 128 as well, which can further aid the supervisor 130 in making decisions about directing the group.

The control/monitoring device 128 can be a device such as a personal computing device (e.g. laptop computer, smartphone, tablet, etc.). In some embodiments the control/monitoring device 128 can represent an abstraction of a number of devices working cooperatively, where, for example, one device acts as a collection point that forwards information to other devices such as a hand-held tablet device used by the supervisor 130, a proprietary server, a cloud server, and other devices. Likewise, the supervisor 130 can represent an abstraction of several individuals who represent different roles, such as, for example, a coach, a medical supervisor, logistics command, and so on, each of which can receive information about members of the group and issue commands to the chin strap biometric sending device of the members of the group, individually or collectively.

Each chin strap biometric device 104 can include sensors for measuring and recording the values of various biometric parameters, such as, for example, pulse rate, blood oxygen level, hydration level, electrocardiogram data, body temperature, blood pressure, and so on. Such parameters can be sensed at different parts of the body, and are conventionally sensed at the chest, wrist, and lower leg. However, it has been found by applicants that the chin is a particularly suitable location for sensing several biometric parameters, and furthermore, biometric sensors can be integrated into a chin strap device, which is ideal for many types of group activities where the group members wear headgear including a chin strap. In some embodiments, by using a chin strap location, circuitry in the chin strap biometric sensing device can be interfaced with circuitry in a helmet worn by the user, which protects the user's head, but also circuitry disposed in the helmet. In addition to biometric, and in some embodiments, environmental sensing, the chin strap biometric sensing device contains a network transceiver to allow communication via electromagnetic (i.e. radio) waves over short distances using a mesh network. A mesh network, as referred to herein, is a dynamic low power wireless ad-hoc network that is a self-organizing, self-healing radio communications network. Each chin strap biometric sensing device acts as a node in the mesh network, and is mobile. As such, routing tables used in conventional mesh networks, where the nodes are generally stationary, are not used. Network associations between nodes can form and break randomly as group members move closer to and farther away from each other due to the low power of the wireless links. Such a mesh network can be implemented using existing wireless networking technologies, such as, for example, the Bluetooth 4.x platform, as specified at http://www.bluetooth.org as of the time of filing the present application and its related priority application. Those skilled in the art will readily appreciate upon reading the instant disclosure that other similar radio networking technologies can similarly be used to implement a suitable mesh network. Each node in a mesh network contends with ad hoc connections and disconnections so that information can be forwarded or relayed among devices (i.e. nodes of the network) to an endpoint, such as the control/monitoring device 128.

As an example of mesh network operation as contemplated herein, device 104 can detect that the chin strap device worn by group member 116 is within range of its wireless transceiver, and transmit a message 114 to the chin strap device worn by group member 116. In turn group member's 116 device can detect that group member's 120 chin strap device is in range and forward the message to the chin strap device worn by group member 120, continuing on as such to the chin strap devices worn by group members 122 and 124. Group member 124 is in range of the control/monitoring device 128, and forwards the message originated by the chin strap device 104 to the control/monitoring device 128 in communication 126, which can also include messages from the chin strap devices of group members 116, 118, 120, 122, and 124. Thus, messages are communicated in a mesh network among group members to eventually relay messages to a network endpoint such as control/monitoring device 128.

Each chin strap device (e.g. 104) follows a mesh network protocol that dictates whether it forwards a message or not. For example, all messages can have an identifier generated by the originating node. Each chin strap device maintains a list of message identifiers it has received and forwarded. If a message is received at a device that has already received and forwarded once, the candidate receiving device can refuse the message, forcing the transmitting node to transmit the message only to a chin strap device or node that has not already forwarded the message once, thereby eliminating repeat transmissions in the network. Alternatively, a limited number of repeat transmissions can be allowed where, for example, each chin strap device maintains a record of the number of times a given message (based on message identifier) as forwarded a message, and if the present number of transmissions for the given message is lower than a preselected number than the device can accept the message, or indicate acceptance if the message is stored, and forward the message again until the maximum number of repeat transmissions is reached.

Messages from the control/monitoring device 128 can also be transmitted to specific nodes (e.g. chin strap biometric sensing device). For example, a command message can be sent from the control/monitoring device 128 to the chin strap device worn by group member 124 as indicated by transmission 132. Group member 124 may, by then, be in mesh network range of group member 116, so the message is forwarded to the chin strap device worn by group member 116 as indicated by transmission 134. When group member 116 is then in mesh network range of group member 102, the chin strap device worn by group member 116 can forward the message to chin strap device 104 as indicated by transmission 136. Thus, the mesh network operates in both directions. Chin strap devices worn by group members can send information, including collected biometric parameter values, to the control/monitoring device 128 or an equivalent mesh network endpoint device. Likewise, messages, such as commands, can be sent to the devices worn by group members. For example, rather than being self-reporting, as in some embodiments, devices such as device 104 can hold and refresh information locally until receiving a polling command from the control/monitoring device 128 (or an equivalent). In response to the polling command, the device then transmits information back through the mesh network to the control/monitoring device 128. Furthermore, messages can traverse the mesh network using different paths (e.g. node hops) as the physical arrangement of the nodes changes during the course of the group activity.

The chin strap biometric sensing device 104 can interface with remotely worn sensors that are worn on other parts of the group member's body in some embodiments. For example, a leg sensor device 106 can communicate with chin strap device 104 over a local wireless link 110, and a wrist sensor device 108 can communicate with chin strap device 104 over a local wireless link 112. The local wireless links 110, 112 can be made using the transceiver of chin strap device 104, or some other short range wireless communication radio circuitry and protocol such as, for example, a personal area network (PAN) such as that specified in the Institute of Electrical and Electronic Engineers (IEEE) specification 802.15.4, which is implemented, for example, under the trade name ZigBee. Other examples of short range wireless communication technologies that can be used include ISA100.11a, WirelessHART, Body Area Network (BAN) according to IEEE 802.15.6, and MiWi.

In addition to biometric data, performance and environmental data can also be collected and transmitted by the chin strap biometric sensing device 104. For example, location of the group member can be determined and tracked using a global positioning satellite receiver, such as a Global Positioning Satellite (GPS) receiver. Movement of a group member can be tracked, as well as the rate of movement, allowing a distinction to be made between, for example, running, walking, standing still, etc. Therefore, the time spent running, for example, can be tracked, as can the locations of the group member when running, and so on. Such performance data can be placed into context (i.e. in time) with the collected biometric data to give a supervisor an indication of the degree to which the group member is performing. A group member's performance can be affected by, for example, hydration level, temperature, calories expended, and so on, and the supervisor 130 can make decisions such as giving the group member rest, or medical attention if merited. In some embodiments, acceleration information can be tracked, such as impact or shock, particularly to the group member's head, which can be relayed to the supervisor as well. Information relayed to the control/monitoring device 128 can be accumulated at the control/monitoring device 128 to show totals since the commencement of the group activity to allow the supervisor 130 to see, for example, the total time engaged in the activity for each group member, the number of acceleration trauma events, and so on.

Thresholds can be set for any of the sensed parameters or other parameters generated from the sensed parameters (e.g. averages, trends, and totals). If a threshold is exceeded, as determined by the chin strap biometric sensing device 104, the message 114 can be deemed priority message that will be relayed and transmitted through the network with priority over non-priority messages in order to get the data of concern to the supervisor 130 as expeditiously as possible. Thus, biometric and other data produced by a given group member can be communicated and organized by a monitoring device 128 or other such backend equipment for display to a supervisor 130, who can then use the information to identify issues with group members from a health perspective as well as a performance perspective.

Figure 2:
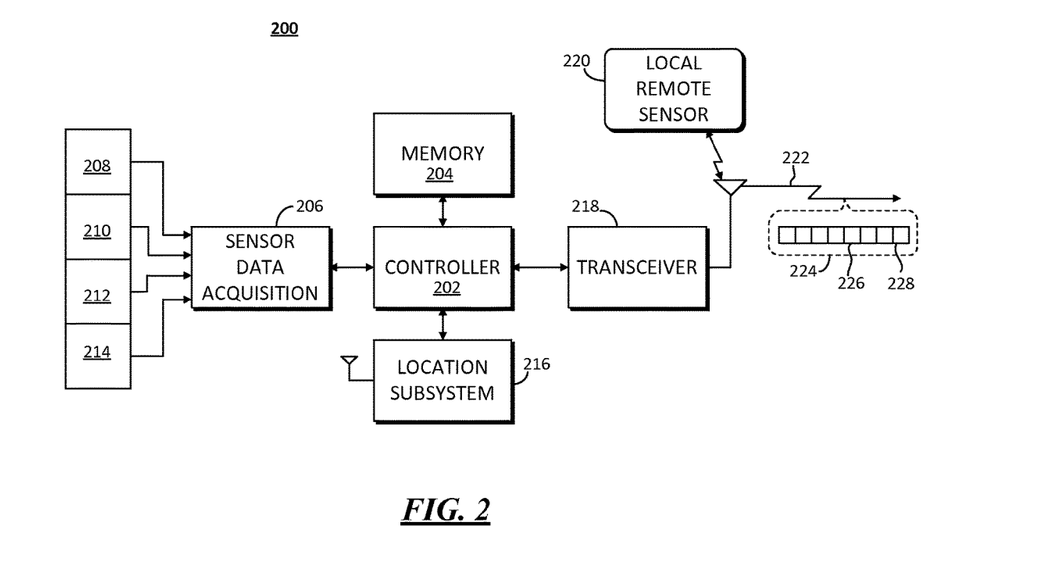
FIG. 2 is block schematic diagram of a chin strap biometric sensing device, in accordance with some embodiments.

FIG. 2 is block schematic diagram of a chin strap biometric sensing device 200, in accordance with some embodiments. The chin strap biometric sensing device 200 senses or measures and collects the values of various biometric parameters, and can sense or measure and collect the values of additional parameters as well. Upon collecting the information, the information can be periodically or occasionally transmitted via a network to a monitoring device for further processing and/or presentation to a person in a supervisory role over the group member wearing the chin strap biometric sensing device. The chin strap biometric sensing device 200 can be implemented in a variety of configurations, including in a chin strap, allowing for the sensing of at least some biometric parameters at the chin of the wearer. The chin strap biometric sensing device 200 is integrated into a chin strap used to hold a helmet or other headgear on a user's head.

Accordingly, the chin strap biometric sensing device 200 includes a controller 202 that controls operation of the chin strap biometric sensing device 200, and which can be a microcontroller or other suitable processing component. The controller 202 can be coupled to an aggregate memory 204 that can include both read only memory (ROM) and random access memory (RAM) for storing and executing instruction code by the controller 202. The memory 204 can include reprogrammable memory, such as flash memory, as well.

The controller 202 can be interfaced with one or more sensor data acquisition circuits 206, which have been abstracted here to a single box. The sensor data acquisition circuit 206 includes circuitry for generally quantifying a sensed parameter, including any necessary analog to digital conversion and signal processing and filtering. A plurality of sensors such as, for example, sensors 208, 210, 212, and 214 can include various types of transducers used to sense various biometric and other parameters, including pulse rate, blood oxygen, temperature, hydration, electrocardiograph or any other biometric parameter that can be electronically detected and sensed. The data representing the various sensed parameters is provided by the sensor data acquisition circuitry 206 to the controller 202. The controller 202 can format a message that includes the biometric data as well as other data. The message can further include an identifier of the chin strap biometric sensing device 200 and a message identifier. The controller 202 can provide the message data to a wireless network transceiver 218 for transmission via a radio signal 222. A transmitted message 224 will therefore include a message identifier 226 the uniquely identifies the message, and a device identifier 228 that uniquely identifies the chin strap biometric sensing device 200. The two identifiers can be combined in one field that includes a message sub-field and a device sub-field. The transmitted message 224 further includes biometric and other collected data, and can contain an indication of priority if the message is a priority message. The transmitted message 224 can be encrypted using an encryption key, and in some embodiments the encryption key can be provided by the control/monitoring device used to supervise all of the chin strap biometric sensing devices in a group. The wireless network transceiver 218 can operate according to a mesh network protocol implemented using a PAN or a BAN network protocol.

The chin strap biometric sensing device 200 can further include a location subsystem circuit 216 that is able to determine a present location of the chin strap biometric sensing device 200. The location subsystem can be, for example, a GPS receiver that produces latitude and longitude coordinate information that can further be used to determine speed. The location information can be included in the transmitted message 224. The location subsystem 216 could further include additional sensors such as accelerometers, gyroscopes and magnetometers to augment the computation of kinematics for a more accurate assessment of parameters such as speed, acceleration and traveled distance.

Furthermore, the chin strap biometric sensing device 200 can interface with remotely worn local sensors 220 that communicate with the controller to provide additional biometric or other data. The local remote sensors can include a sensing transducer and a sensor data acquisition circuit similar to sensors 208-214 and sensor data acquisition circuit 206, respectively. The local remote sensor can be, for example, configured as a wrist strap device, a chest strap device, an ankle device, or in any other configuration suitable for being worn and sending a biometric parameter. The local remote sensor 220 can communicate with the controller 202 via the network transceiver 218, or through another transceiver operating as a PAN or BAN transceiver that is connected to the controller 202 in a similar manner.

In transmitting message 224, the network transceiver can periodically transmit a polling beacon to detect other network nodes within range. When the transceiver 218 detects a response to a polling beacon, it can transmit message 224 to the responding node. The receiving node, if not the endpoint (e.g. monitoring device) of the network can relay the message to another node, which continues on until the message is finally transmitted to the endpoint of the network. Thus, the chin strap biometric sensing device 200 can collect biometric and other information, and relay it via the network to the monitoring device.

Figure 3:
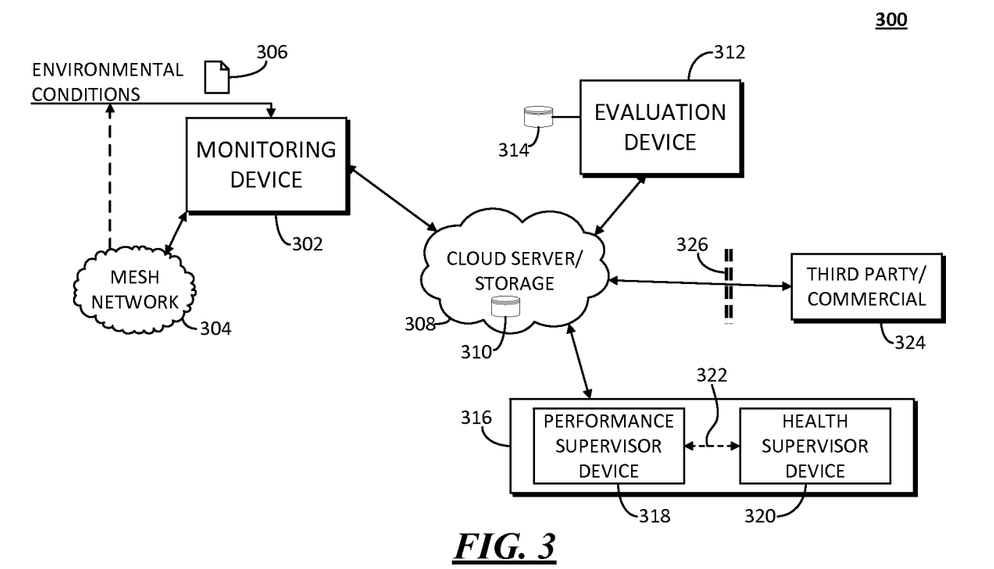
FIG. 3 is a system diagram of a backend of a biometric data collection and evaluation system, in accordance with some embodiments.

FIG. 3 is a system diagram of a backend 300 of a biometric data collection and evaluation system, in accordance with some embodiments. The system of FIG. 1 illustrates a minimal system where the control/monitoring device 128 is abstracted to include evaluation, processing, and presentation capabilities to present processed and formatted data relating to each individual group member to the supervisor 130. These same functions can be distributed, however, in a more sophisticated manner, as in the backend 300, in which a monitoring device 302 receives messages from, and transmits messages to individual chin strap biometric sensing device via a wireless mesh network 304. In addition to the biometric and other data received from the chin strap biometric sensing devices, the monitoring device 302 can further receive environmental condition information 306 that indicates parameters such as, for example, the temperature and humidity of the environment in which the group members are engaging in an activity. Such information can be useful, for example, when considering various health and performance metrics. The monitoring device 302 can be connected to a backend server, such as a cloud server 308 that can provide storage resources 310 in which the biometric and other data received from each group member, and data generated from that data (i.e. trends, averages, totals), can be stored and accessed by other entities. Access to the information stored on the cloud server 308 can be controlled and provided selectively based on the role of the entity accessing the could server 308. For example, and person acting in a medical role can be granted access to private health information for each of the group members, whereas a mere spectator entity (e.g. a fan service) may be allowed access to minimal performance information for particular group members.

An evaluation device 312, which includes computing hardware, can access the biometric data for each group member that is stored in storage resource 310 and evaluate the information to determine if there are any health concerns indicated by the biometric data for a given group member. The evaluation device 312 can compare biometric data for each group member against a member profile that can be stored in a member database 314. The member profile can indicate any health conditions which can modify default health parameter thresholds in determining whether a health concern exists based on a given member's current biometric information. The evaluation device 312 can further develop additional information such as averages, totals, and trends for any biometric parameter so that changes over time can be recorded, tracked, and evaluated as well. The developed information can be stored with the sensed biometric information in the storage resource 310 in correspondence with or as part of the particular group member's record. The evaluation device 312 can maintain a set of default threshold which are used to evaluate biometric parameters in order to identify any potential health concerns in lieu of member-specific thresholds. Upon determining that a biometric parameter, either a sensed or derived parameter, has exceed a threshold, the evaluation device can flag the group member's record, indicating a problem, and further indicating specific parameter that is beyond a threshold. Furthermore, the thresholds can be layered so that a first threshold indicates a concern level and where a second threshold can indicate more urgent attention is required.

A supervisor device or device 316 can be another type of device used for evaluation of group member information, and can access the evaluated and processed data in the storage resource 310 and display it for viewing. In some embodiments, when a given biometric parameter exceeds a threshold, as determined by the evaluation device 312, the evaluation device 312 can forward an alert to the supervisor device 316 for immediate attention. Generally, the supervisor device 316 runs application software designed to periodically or occasionally fetch group member data from the storage resource 310 for display. In some embodiments the group member data can be fetch responsive to an input received at the supervisor device 316. In some embodiments a combination of data fetching schemes can be used where a summary level of data is routinely fetched to maintain sufficient recency of information at the supervisor device, and if the supervisor wants to see more detailed information then the supervisor can provide an input at the supervisor device 316 to cause the supervisor device 316 to fetch the most recent detailed information for an indicated group member.

In some embodiments the supervisor device function can be split among several devices. For example, a coach can use a performance supervisor device 318 for monitoring performance and biometric data of athletes during an athletic event or game, and a doctor or other medical supervisor can monitor more detailed health information at a health supervisor device 320. In some embodiments the performance and health supervisor devices can be substantially identical but with difference options selected to display information more pertinent to each supervisor's role. Furthermore, the various supervisor devices can, in some embodiments, flag or otherwise draw the other supervisor device or devices attention to a particular group member or parameter of a group member via an alert message 322.

In some embodiments a portion of the group member data in storage resource 310 (or a similar storage resource) can be made available to third parties 324 through a firewall 326. Examples of third parties can include, for example, fans of a sports team (the team being the group). Certain data for each group or team member can be made available under a subscription agreement in some embodiments, allowing fans to see real or near real time data for players. Access to some information regarding group members can be provided as a service to, for example, fans or spectators as a pay per view or paid subscription service.

Figure 4:
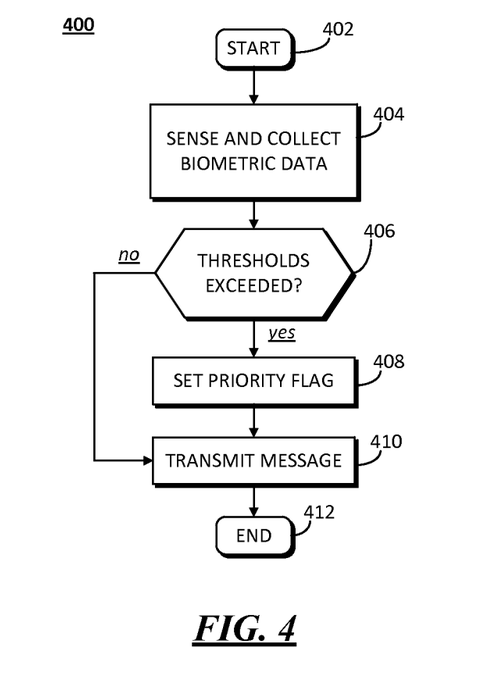
FIG. 4 is a flow chart diagram of a method for collecting biometric data at a chin strap biometric sensing device, in accordance with some embodiments.

FIG. 4 is a flow chart diagram of a method 400 for collecting biometric data at a chin strap biometric sensing device, in accordance with some embodiments. The chin strap biometric sensing device can be, for example, a device substantially similar to that of device 200, and is worn on a group member's body, such as in a chin strap, wrist strap, chest strap, or other similar body mounting configuration. At the start 402 the chin strap biometric sensing device is (battery) powered on and affixed to a group member's body, with electrodes and other sending transducers properly placed to sense various biometric parameters as previously described. In step 404 the sensor data acquisition circuit for each transducer produces a signal value from its respective sensor transducer to produce biometric data.

In some embodiments the chin strap biometric sensing device can include one or more default threshold values for the various sensed or derived parameters. In step 406 the controller of the chin strap biometric sensing device can compare sensed parameters to the default threshold, and if any sensed parameter exceeds a default threshold, then in step 408 the controller can flag a data message including the sensed parameter whose value exceeds the default parameter for priority. If no sensed parameter exceeds a default threshold, then the method can proceed from step 406 to step 410 where the message including sensed parameters is transmitted using the mesh network protocol. The message is also formatted to include an identifier associated with the chin strap biometric sensing device, as a unique or serialized message identifier to uniquely identify the message. Accordingly, to transmit the message the network transceiver of the chin strap biometric sensing device first attempts to find a candidate device (i.e. another chin strap biometric sensing device or monitoring device) to which the message can be transmitted, and upon finding such a candidate device, the message is transmitted to the candidate device, at which time the method 400 (for the present iteration) ends 412. The method 400 is generally repeated periodically or occasionally so that timely updates of information will be transmitted to the monitoring device. It will be appreciated by those skilled in the art that the information transmitted in step 410 can include data in addition to biometric data, such as, for example, location data that is also produced by circuitry of the chin strap biometric sensing device.

Figure 5:
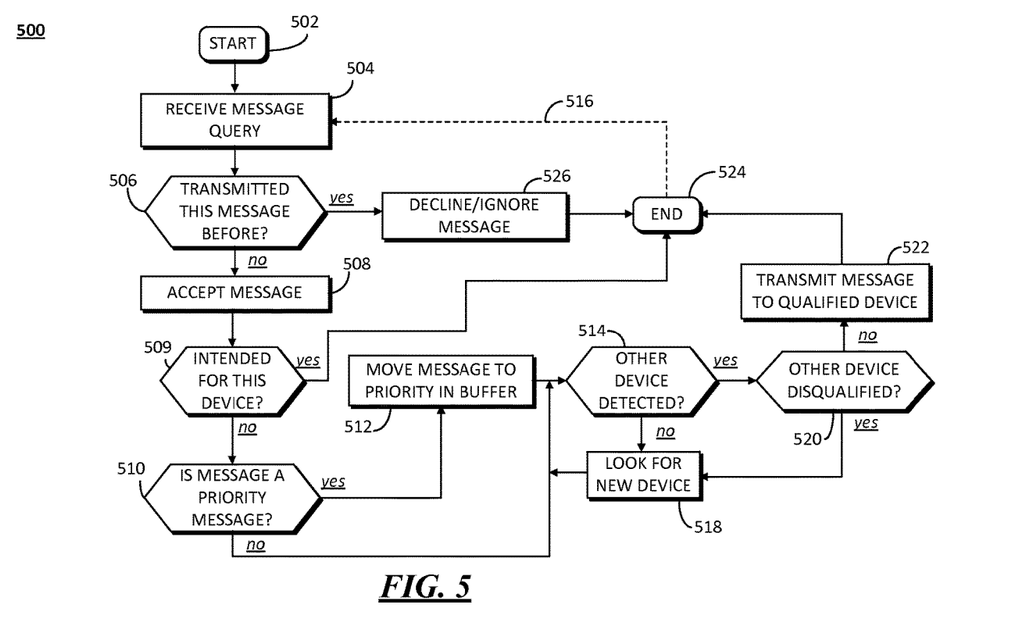
FIG. 5 is a flow chart for a method of processing a bidirectional message at a node in a network, in accordance with some embodiments.

FIG. 5 is a flow chart for a method 500 of processing a message at a node in the wireless mesh network, in accordance with some embodiments. The method 500 illustrates embodiments of relaying a message including biometric data in the wireless mesh network. That is, the method is performed by a chin strap biometric sensing device that is not the originator of the data in the message being relayed, or attempting to be relayed from another chin strap biometric sensing device, which itself may or may not be the originator of the data in the message. An important aspect of the wireless mesh network is that messages are either not re-transmitted by any node in the wireless mesh network (i.e. transmitted only once), or they are re-transmitted only a limited number of times in order to prevent an undue number of transmissions in it. In general, a node (e.g. one of the chin strap biometric sensing devices) that has a message to be transmitted can periodically transmit a polling beacon to detect nearby nodes, or to advertise their presence. Nodes with original messages to be transmitted can connect to another node, and transmit the message. The receiving node can log the message identifier so that, in the future, it does not accept or re-transmit the message more than the limited number of times allowed, which can be just once. If, in the future, a node is queried by another node, the querying node can transmit the message identifier to the candidate receiving node so that the candidate receiving node can determine if it has already transmitted the message the maximum number of times allowed. If so, the candidate receiving node replies with a decline message, otherwise it responds with an affirm message and receives the message from the transmitting node.

Accordingly, at the start 502, a given node, which is one of the plurality of chin strap biometric sensing devices, is powered on. In order to be discoverable, the node can periodically transmit a beacon to advertise its presence to other nearby nodes. In step 504 the node receives a query message from another node with a message that it is attempting to transmit. The message contains an identifier or some other means of uniquely identifying the message (e.g. originator identifier and time stamp). The node, in step 506, evaluates the proposed message identifier to determine whether the node has handled the identified message before (at least the maximum number of times, which in this example is once). If the node has already transmitted the message, the method 500 proceeds to step 526 where the node can respond with a decline message, or simply not respond at all, at which point the method ends 524, and may be repeated as indicated by dashed line 516.

If, in step 506, the node determines that it has not transmitted the message before, it will respond in step 508 and accept the message, whereupon the querying node will forward the message. Upon receiving the message, in step 509, the receiving node determines if the message is intended for the receiving node, such as when the supervisor sends a message to one or more of the group members' devices. If the message is intended for the receiving node then the method ends 524 and the receiving node processes the message (which can prompt a reply). If the message is not intended for the receiving node, the message is to be forwarded in the mesh network by the receiving device, and the method 500 proceeds to step 510 where the method 500 determines whether the message is a priority message. If the received message is a priority message, then the message is given priority position in the receiving node's message buffer in step 512. If the message is determined to not be a priority message in step 510, or after giving the message its due priority status in step 512, the method 500 proceeds to step 514 where the receiving node attempts to forward the message to another node in the mesh network. In step 514 the receiving node can attempt to locate another node to which the message can be forwarded. Once another node is detected the method 500 proceeds to step 520 where the detected node is qualified in the same way the node performing method 500 was qualified in steps 504, 506. The node transmits the message identifier to a detected node, which then responds with either an acceptance acknowledgement, an express denial, or no response. In step 520, if the detected device is not qualified, meaning it has already transmitted the message the maximum allowed number of times, the method 500 can seek to detect another node (device) in step 518 such as by, for example, detecting a beacon advertising the presence of another node. If the originally detected node accepts (i.e. is qualified) in step 520, then the method 500 proceeds to step 522 where the message is transmitted to the detected node, and the method, for the present message, ends 524. It will be appreciated by those skilled in the art that variations on the steps indicated can be implemented without departing from the goal of promulgating the message through the network eventually to the monitoring device as the endpoint.

Figure 6:
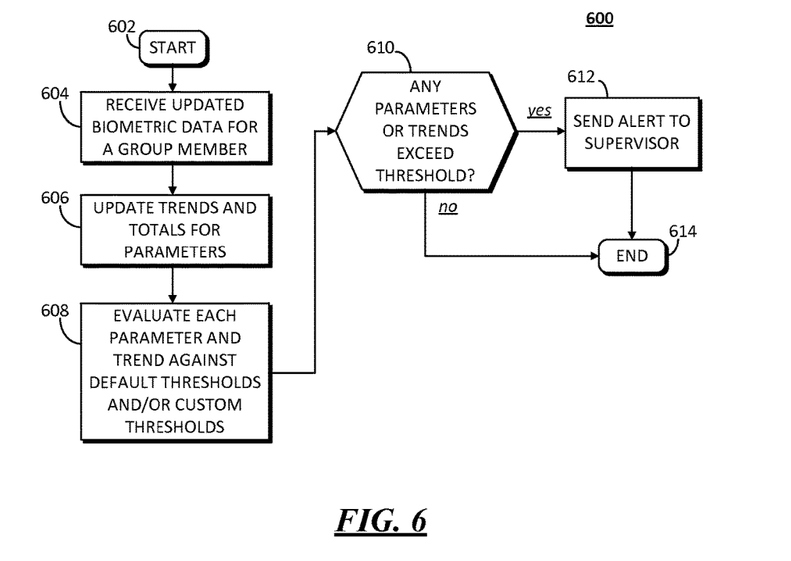
FIG. 6 is a flow chart of a method for evaluating biometric data, in accordance with some embodiments.

FIG. 6 is a flow chart of a method 600 for evaluating biometric data, in accordance with some embodiments. The method 600 can be performed by, in some embodiments, the monitoring device 128 of FIG. 1, and in some embodiments by an evaluation device in a backend system such as evaluation device 312 of FIG. 3, or any other suitable device capable of comparing biometric data of a group member with a set of default thresholds or modified thresholds for the particular group member. At the start 602 the device performing the evaluation is on and able to accept biometric data for group members. This can occur by receiving data from the plurality of chin strap biometric sensing devices through the network, or the data can be fetched from a server where the data is placed by a monitoring device and stored. In general, the data is stored in records where each record corresponds to one of the chin strap biometric sensing devices and is associated with the particular group member wearing the chin strap biometric sensing device. The records can include the most recent biometric data obtained from the chin strap biometric sensing device, as well as derived data produced from the sensed data produced by the chin strap biometric sensing device. The derived data can include, for example, an average of a given biometric parameter or a total for a performance parameter produced over a time period. The records can be associated with profiles for each group member that can specify modified thresholds for particular biometric parameters to be used instead of default threshold based on a known health condition of the group member.

Accordingly, in step 604, for a given iteration of the method 600, updated biometric data, and other data such as performance data, if available, can be received and made accessible to an evaluation device or an evaluation function. In step 606 any running or derived parameters can be updated with the data received in step 604. In step 608 the recently received and updated data is evaluated against the default or alternative threshold(s) custom to the particular group member whose data is being evaluated. In step 610 any thresholds that are exceeded are noted. If any thresholds are exceeded, then in step 612 and alert can be sent to an appropriate supervisor to draw attention to the group member's data and the particular parameter that has exceeded the applicable threshold. Once the data has been evaluated, the method ends 614 for the present iteration, and the method 600 can be repeated as necessary, and when updated biometric data and other parameter values are received.

Figure 7:
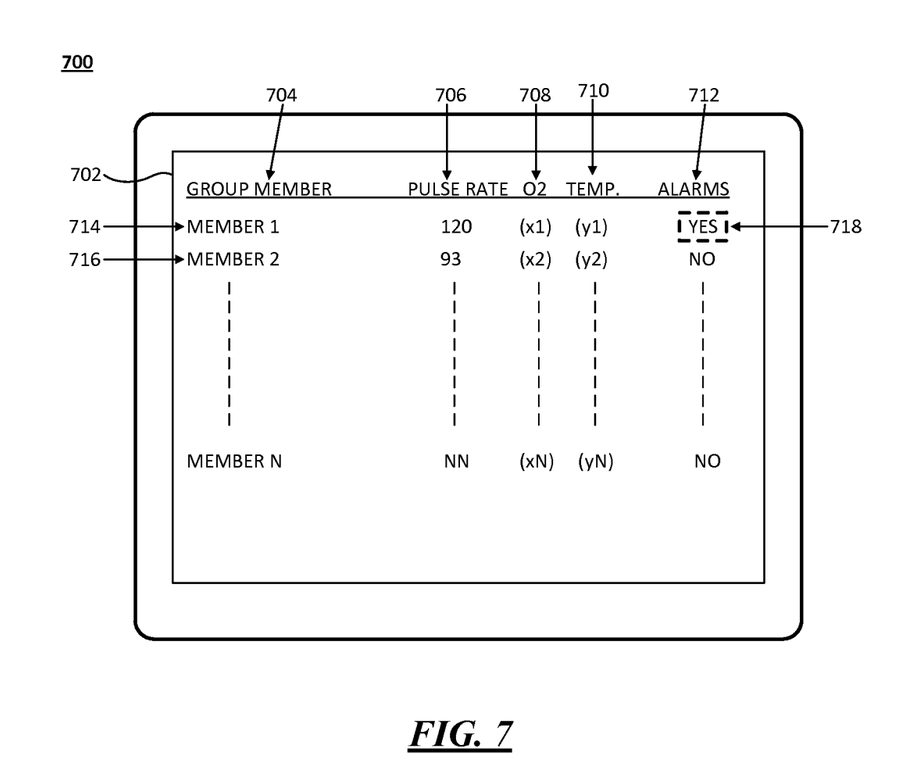
FIG. 7 is a user interface for displaying collected and processed biometric data for members of a group, in accordance with some embodiments.

FIG. 7 is a user interface 700 for displaying collected and processed biometric data for members of a group, in accordance with some embodiments. The user interface can be presented on a graphical display of a computing device, such a personal computer, and laptop computer, a tablet device, and so on, and presents formatted data received and derived from data transmitted by each group member's respective chin strap biometric sensing device. Accordingly, a window 702 can represent an application window of an application or program designed to acquire and display collected and derived data. In the window 702 the user interface 700 can provide, for example, headings for different categories or fields, including a group member name or identifier 704, a most recent pulse rate parameter value 706, a most recent blood oxygen parameter value 708, a most recent temperature parameter value 710, and an alarm field 712 to indicate whether the applicable thresholds for any of the parameters have been exceeded. Rows of the user interface 700 can include the information associated for each of several group members such as group members 714, 716, and their corresponding data for each displayed category. The user interface 700 can be configurable so that different parameters can be selected for display, and it can be dynamic so that parameter values are updated as new data is received for the group members whose data is being presented in the user interface 700. An alarm can be indicated as present at alarm field 718, for example, indicating one or more of the respective group member's parameter values is outside of an acceptable or preferred range. Alternatively an alarm can be indicated by the color of the parameter value being displayed in a given field (e.g. red indicates a parameter that exceeds an applicable threshold). In some embodiments the alarm can indicate the potential of a concussion due to an acceleration parameter measured at the chin strap biometric sensing device exceeding an acceptable acceleration threshold.

Any field can be made "clickable" so that, upon being selected, additional and more detailed data is presented in the user interface 700 that is pertinent to the selected parameter. In some embodiments there can be several instances of user interfaces such as user interface 700, and the different instances of the user interfaces can be configured to suit the role of a particular supervisor using the user interface. For example, a user interface emphasizing health-related parameters can be configured for a health supervisor (e.g. 320 of FIG. 3) and a user interface emphasizing performance-related parameters can be provided to a performance supervisor (e.g. 318 of FIG. 3).

The various embodiments of the disclosure provide the benefit of allowing those in a supervisory role over a group engaged in an activity to see near-real time biometric and other data for members of the group during the activity so as to identify health concerns that the group member may not be aware, without unduly interrupting the activity. The data can further provide the benefit of monitoring group member performance during the activity so that decisions about group member participation, for example, can be made by the supervisor. By utilizing a network, the chin strap biometric sensing devices can be kept small, and information can be relayed from group member to group member until it reaches the monitoring device in sufficient time that the data presented to the supervisor(s) is timely and significant.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

It will be appreciated that some embodiments may be comprised of one or more generic or specialized processors (or "processing devices") such as microprocessors, digital signal processors, customized processors and field programmable gate arrays (FPGAs) and unique stored program instructions (including both software and firmware) that control the one or more processors to implement, in conjunction with certain non-processor circuits, some, most, or all of the functions of the method and/or apparatus described herein. Alternatively, some or all functions could be implemented by a state machine that has no stored program instructions, or in one or more application specific integrated circuits (ASICs), in which each function or some combinations of certain of the functions are implemented as custom logic. Of course, a combination of the two approaches could be used.

Moreover, an embodiment can be implemented as a computer-readable storage medium having computer readable code stored thereon for programming a computer (e.g., comprising a processor) to perform a method as described and claimed herein. Examples of such computer-readable storage mediums include, but are not limited to, a hard disk, a CD-ROM, an optical storage device, a magnetic storage device, a ROM (Read Only Memory), a PROM (Programmable Read Only Memory), an EPROM (Erasable Programmable Read Only Memory), an EEPROM (Electrically Erasable Programmable Read Only Memory) and a Flash memory. Further, it is expected that one of ordinary skill, notwithstanding possibly significant effort and many design choices motivated by, for example, available time, current technology, and economic considerations, when guided by the concepts and principles disclosed herein will be readily capable of generating such software instructions and programs and ICs with minimal experimentation.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description as part of the original disclosure, and remain so even if cancelled from the claims during prosecution of the application, with each claim standing on its own as a separately claimed subject matter. Furthermore, subject matter not shown should not be assumed to be necessarily present, and that in some instances it may become necessary to define the claims by use of negative limitations, which are supported herein by merely not showing the subject matter disclaimed in such negative limitations.

We claim:

1. A network-based biometric collection and reporting system for a group, comprising:
a plurality of biometric chin strap sensing devices, each configured to be worn by a member of the group and to collect biometric data of the respective members of the group, and each including a wireless transceiver, wherein each of the plurality of chin strap biometric sensing devices transmits and relays collected biometric data via a wireless mesh network established by the plurality of chin strap biometric sensing devices; and
a monitoring device in communication with the wireless mesh network that receives the biometric data of each member of the group via the wireless mesh network in a generally real time manner and organizes the biometric data for display to a supervisor of the group by group member.

2. The system of claim 1, wherein the organized biometric data is transmitted to a supervisor device by the monitoring device, wherein the supervisor device operates a user interface to allow the supervisor of the group to view the organized biometric data for each group member.

3. The system of claim 1, wherein each biometric sensing device is further configured to collect performance data of the respective member and transmit the performance data with the biometric data, the monitoring device organizes the biometric data and performance data for each member of the group into a health category and a performance category.

4. The system of claim 3, wherein the organized biometric data in the health category is transmitted to a health supervisor device by the monitoring device, wherein the organized performance data in the performance category is transmitted to a performance supervisor device, and wherein the health and performance supervisor devices each operate a user interface to allow a respective supervisor of the group to view the organized biometric and performance data for each group member.

5. The system of claim 1, wherein the monitoring device further includes a health database including health information for at least some of the group members and evaluates received biometric device for each of the at least some group members in view of the respective health information to identify health issue when the biometric data exceeds one or more health thresholds.

6. The system of claim 1, wherein, each of the plurality of chin strap biometric sensing devices is configured to periodically sense the biometric parameters and transmit them, each of the plurality of chin strap biometric sensing devices is further configured to transmit the biometric parameters in a priority message to the monitoring device via the wireless mesh network in response to detection of biometric parameters of the respective group member that exceeds a preselected threshold, and wherein the priority message, when transmitted in the wireless mesh network, is transmitted before non-priority messages in the wireless mesh network.

7. The system of claim 3, wherein the performance data collected by each of the plurality of wearable biometric sensing devices includes acceleration data of the respective group member.

8. The system of claim 1, wherein each of the plurality of chin strap biometric sensing devices further includes location detecting sub-system and reports information derived from its location along with the biometric data.

9. The system of claim 1, further comprising, for each one of the plurality of chin strap biometric sensing devices, a plurality of additional sensors for sensing biometric parameters at different locations of the respective group member's body, and wherein each of the plurality of additional sensors are in communication with a control module that includes the wireless transceiver.

10. The system of claim 1, wherein each of the plurality of chin strap biometric sensing devices is attached to a helmet used by a respective user of each chin strap biometric sensing device.

11. The system of claim 1, wherein the wireless mesh network is an ad hoc wireless mesh network.

12. The system of claim 1, wherein the wireless network is a first wireless mesh network and the plurality of chin strap biometric sensing devices is a first plurality of chin strap biometric sensing devices, the monitoring device is further in communication with a second wireless mesh network comprised of a second plurality of chin strap biometric sensing devices, and receives biometric data from the second plurality of biometric device that is organized by the monitoring device for display to a supervisor of the second plurality of chin strap biometric sensing devices.

13. A method, comprising:
sensing at least one biometric parameter to produce biometric data at each of a plurality of chin strap biometric sensing devices, wherein the plurality of chin strap biometric sensing devices form a wireless mesh network;
each of the plurality of chin strap biometric sensing devices transmitting collected biometric data from a user wearing the respective chin strap biometric sensing device through the wireless mesh network to a monitoring device; and
organizing the biometric data received at the monitoring device from each of the plurality of chin strap biometric sensing devices for display to a supervisor.

14. The method of claim 13, wherein transmitting the collected biometric data is performed in response to a message received from the monitoring device through the wireless mesh network.

15. The method of claim 13, further comprising:
sensing at least one performance parameter to produce performance data at each of the plurality of wearable biometric sensing devices,
categorizing the biometric data and performance data received by the monitoring device into biometric and performance categories, respectively; and
providing the biometric and performance categories of the biometric and performance data to respective different entities.

16. The method of claim 13, wherein transmitting the collected biometric data includes encrypting the collected biometric data by each of the plurality of wearable biometric sending devices.

17. The method of claim 16, wherein encrypting the collected biometric data is performed responsive to receiving an encryption key from the monitoring device.

18. A chin strap biometric sensing device, comprising:
a wireless network transceiver configured to operate the chin strap biometric sensing device as a node in a wireless dynamic mesh network;
at least one biometric sensor that senses a biometric parameter at a chin of a user of the chin strap biometric sensing device to produce a biometric parameter value; and
a sensor data acquisition circuit that quantifies the sensed biometric parameter;
wherein the wireless network transceiver transmits biometric parameter value via the wireless dynamic mesh network to an endpoint device of the dynamic mesh network.

19. The chin strap biometric sensing device of claim 18, further comprising:
a location subsystem that produces location information indicating a location of the chin strap biometric sensing device; and
wherein the wireless network transceiver transmits the location information via the wireless dynamic mesh network to an endpoint device of the dynamic mesh network.

20. The chin strap biometric sensing device of claim 18, wherein the wireless network transceiver transmits the biometric parameter value in response to a command received via the dynamic mesh network at the wireless network transceiver.

* * * * *